United States Patent
Holmes et al.

(10) Patent No.: US 9,495,737 B2
(45) Date of Patent: Nov. 15, 2016

(54) THERMAL SOUND INSPECTION SYSTEM

(71) Applicant: The Boeing Company, Chicago, IL (US)

(72) Inventors: Tyler M. Holmes, Seattle, WA (US); Jeffrey G. Thompson, Auburn, WA (US); Jeffrey Reyner Kollgaard, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 413 days.

(21) Appl. No.: 13/664,777

(22) Filed: Oct. 31, 2012

(65) Prior Publication Data
US 2014/0118530 A1    May 1, 2014

(51) Int. Cl.
| | |
|---|---|
| *G01N 21/00* | (2006.01) |
| *G06T 7/00* | (2006.01) |
| *G01N 25/72* | (2006.01) |
| *G01N 29/04* | (2006.01) |
| *G01N 29/22* | (2006.01) |
| *H04N 7/18* | (2006.01) |
| *G06K 9/00* | (2006.01) |

(52) U.S. Cl.
CPC .............. *G06T 7/0004* (2013.01); *G01N 25/72* (2013.01); *G01N 29/04* (2013.01); *G01N 29/22* (2013.01); *G01N 2291/2694* (2013.01); *G06T 2207/10016* (2013.01); *G06T 2207/10048* (2013.01); *G06T 2207/20221* (2013.01); *G06T 2207/30164* (2013.01)

(58) Field of Classification Search
CPC .............. H04N 7/18; H04N 5/33; G06K 9/00; G06K 9/6202; G01N 25/72; G01N 29/06; G01N 29/04; G01N 29/22; G06T 7/00; G06T 2207/10016; G06T 2207/10048; G06T 2207/20221; G06T 2207/30164; G06T 7/0004; G06T 7/0046; G06T 7/0048
USPC ........... 348/33, 34, 162, 163, 125, 192, 130, 348/141, 92, 94; 250/339.11, 338.1, 341.8
See application file for complete search history.

(56) References Cited

U.S. PATENT DOCUMENTS

| | | | | |
|---|---|---|---|---|
| 3,416,857 | A | * 12/1968 | Lookabaugh | .......... A61B 3/024 351/224 |
| 3,745,814 | A | * 7/1973 | Gabor | .................. A61B 8/0825 359/901 |

(Continued)

FOREIGN PATENT DOCUMENTS

| | | |
|---|---|---|
| EP | 1431755 A2 | 6/2004 |
| EP | 2653828 A1 * | 10/2013 |
| WO | WO2006124977 A2 | 11/2006 |

OTHER PUBLICATIONS

"TAMARISK 320", DRS Technologies, A Whole New Dimension in Thermal Imaging Performance, DRS RSTA, Inc., Copyright 2011, 2 pages.

(Continued)

*Primary Examiner* — Richard Torrente
*Assistant Examiner* — Marnie Matt
(74) *Attorney, Agent, or Firm* — Yee & Associates, P.C.

(57) ABSTRACT

A method and apparatus for inspecting a structure. Images of heat generated by an inconsistency in the structure are received. A final image is generated from the images using portions of the images having a greatest amount of heat.

22 Claims, 11 Drawing Sheets

(56) References Cited

U.S. PATENT DOCUMENTS

| | | | | |
|---|---|---|---|---|
| 5,444,241 A * | 8/1995 | Del Grande | | G01N 25/72 250/253 |
| 5,655,030 A * | 8/1997 | Suzuki | | G06T 7/602 348/95 |
| 5,771,309 A * | 6/1998 | Yamaoka | | G01B 11/002 348/94 |
| 6,154,279 A * | 11/2000 | Thayer | | G01B 11/24 356/602 |
| 7,075,084 B2 | 7/2006 | Thompson et al. | | |
| 7,716,987 B2 * | 5/2010 | Sathish | | G01N 25/72 250/341.1 |
| 8,914,744 B2 * | 12/2014 | Spencer | | G06F 3/14 715/800 |
| 2004/0051035 A1 * | 3/2004 | Zombo | | G01N 25/72 250/252.1 |
| 2004/0089811 A1 * | 5/2004 | Lewis | | G01N 25/72 250/341.6 |
| 2004/0119019 A1 * | 6/2004 | Thompson | | G01N 25/72 250/341.6 |
| 2008/0148863 A1 * | 6/2008 | Thompson | | G01M 5/005 73/788 |
| 2009/0060666 A1 * | 3/2009 | Georgeson | | B23B 35/00 408/16 |
| 2010/0019153 A1 * | 1/2010 | Zalameda | | G01N 25/72 250/339.02 |
| 2011/0166824 A1 * | 7/2011 | Haisty | | G01B 5/12 702/157 |
| 2013/0250719 A1 * | 9/2013 | Kollgaard | | G01N 27/90 367/7 |

OTHER PUBLICATIONS

Combined Search and Examination Report, dated Apr. 30, 2014, regarding Application No. GB1319272.9, 6 pages.

* cited by examiner

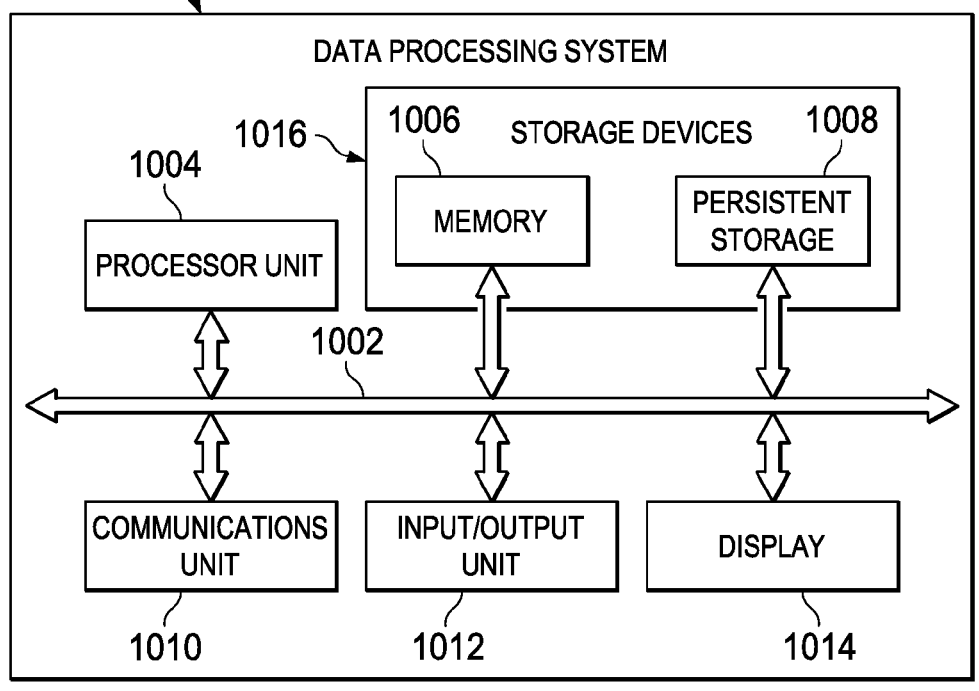
FIG. 10
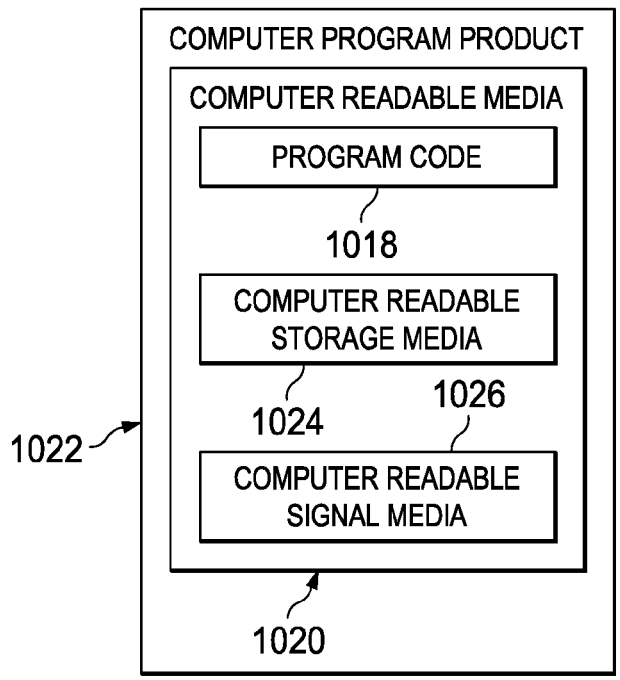

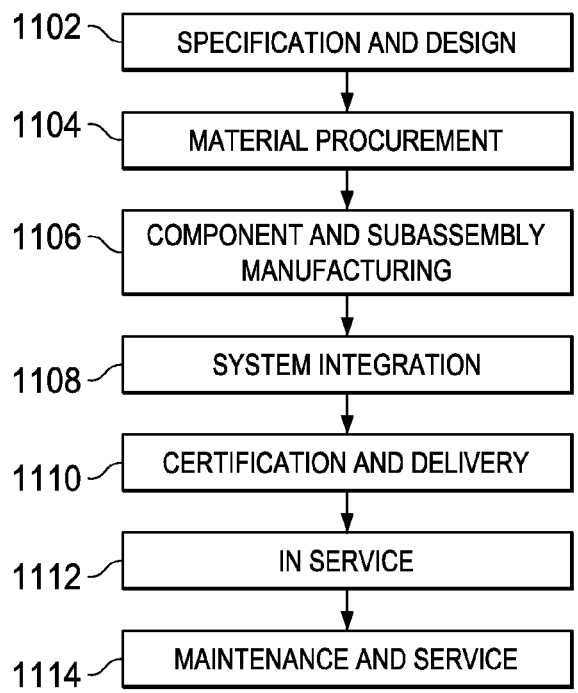
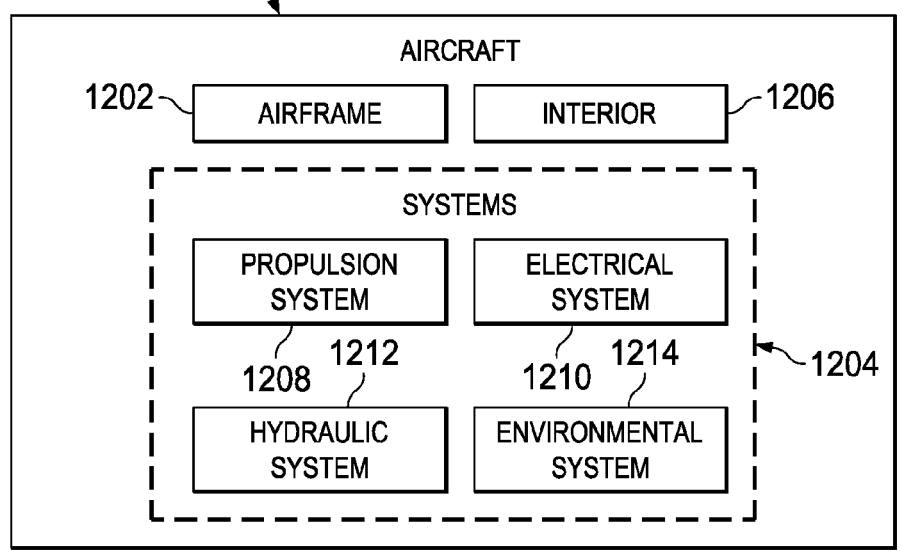

THERMAL SOUND INSPECTION SYSTEM

BACKGROUND INFORMATION

1. Field

The present disclosure relates generally to inspecting structures and, in particular, to inspecting countersinks in structures. Still more particularly, the present disclosure relates to a method and apparatus for identifying inconsistencies in countersinks formed in a composite structure.

2. Background

Aircraft are being designed and manufactured with greater and greater percentages of composite materials. Composite materials are used in aircraft to decrease the weight of the aircraft. This decreased weight improves performance features such as payload capacities and fuel efficiencies. Further, composite materials provide longer service life for various components in an aircraft.

Composite materials are tough, light-weight materials created by combining two or more functional components. For example, a composite material may include reinforcing fibers bound in polymer resin matrix. The fibers may be unidirectional or may take the form of a woven cloth or fabric. The fibers and resins are arranged and cured to form a composite material.

Further, using composite materials to create aerospace composite structures potentially allows for portions of an aircraft to be manufactured in larger pieces or sections. For example, a fuselage in an aircraft may be created in cylindrical sections and then assembled to form the fuselage of the aircraft. Other examples include, without limitation, wing sections joined to form a wing or stabilizer sections joined to form a stabilizer.

In manufacturing composite structures, layers of composite material are typically laid up on a tool. The layers may be comprised of fibers in sheets. These sheets may take the form of fabrics, tape, tows, or other suitable forms. In some cases, resin may be infused or pre-impregnated into the sheets. These types of sheets are commonly referred to as prepreg.

The different layers of prepreg may be laid up in different orientations and different numbers of layers may be used depending on the thickness of the composite structure being manufactured. These layers may be laid up by hand or using automated lamination equipment such as a tape laminating machine or a fiber placement system.

After the different layers of composite material have been laid up on the tool, the layers of composite material may be consolidated and cured upon exposure to temperature and pressure, thus forming the final composite structure.

Thereafter, the composite structure may be inspected using a nondestructive inspection system to determine whether inconsistencies are present. These types of nondestructive inspection systems also may be used to inspect the composite structure after the composite structure has been processed for assembly. For example, an inspection may be performed after holes are formed in the composite structure. The formation of holes and other features such as countersinks may result in the formation of inconsistencies in the composite structure.

If an inconsistency is identified, the composite structure may be reworked. In some cases, the inconsistency may result in the composite structure being discarded, requiring a new composite structure to be manufactured. Examples of inconsistencies that may be present in a composite structure include voids, porosity, delamination, foreign object debris, and other types of inconsistencies.

Nondestructive inspection involves different analysis techniques used to evaluate the properties of an object without causing damage to the object. Nondestructive inspection may be performed in a number of different ways.

For example, nondestructive inspection may include ultrasonic testing. Ultrasonic testing involves using sound waves to inspect objects. The object tested may be comprised of different types of materials. For example, the materials may be one of steel, metals, alloys, concrete, wood, composite materials, and other types of materials.

With ultrasonic inspection, ultrasonic transducers may be used to perform the ultrasonic inspection of the structure. Ultrasonic transducers cause sound signals to travel through a structure, such as a composite structure. The responses detected from the sound signals may be used to identify a location of an inconsistency. However, this type of inspection may not provide as much information about the inconsistency as desired.

For example, the depth of an inconsistency may not be as easily detectable beyond the first delamination encountered by the sound signals. Responses to ultrasonic sound signals encountering these inconsistencies near holes, countersinks, and other features may not provide information that is as accurate as desired with currently used pulse echo ultrasonic inspection techniques.

For example, the depth of an inconsistency in a countersink, such as a delamination, formed in the surface of an object may not be as easily detectable beyond the first inconsistency encountered by the ultrasonic sound signals. A shadowing effect of a delaminated layer located over other delaminated layers in the inconsistency within the countersink is present in a pulse echo ultrasonic inspection of the countersink. The ultrasonic sound signals are reflected at the first delaminated layer in the inconsistency. As a result, other delaminated layers below the first delaminated layer encountered on the countersink may not be identifiable from the response to the sound signals.

Therefore, it would desirable to have a method and apparatus that takes into account at least some of the issues discussed above as well as possibly other issues.

SUMMARY

In one illustrative embodiment, an apparatus comprises a sound signal generator, a camera system, and an image generator. The sound signal generator is configured to generate sound signals in a structure. The camera system is configured to detect heat and generate image data about the heat. The image generator is configured to receive images from the camera system and generate a final image using areas of the images having a greatest amount of heat.

In another illustrative embodiment, a method for inspecting a structure is present. Images of heat generated by an inconsistency in the structure are received. A final image is generated from the images using areas of the images having a greatest amount of heat.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 10 is an illustration of a block diagram of a data processing system in accordance with an illustrative embodiment;

FIG. 11 is an illustration of an aircraft manufacturing and service method in accordance with an illustrative embodiment; and FIG. 12 is an illustration of an aircraft in which an illustrative embodiment may be implemented.

DETAILED DESCRIPTION

Figure 1:
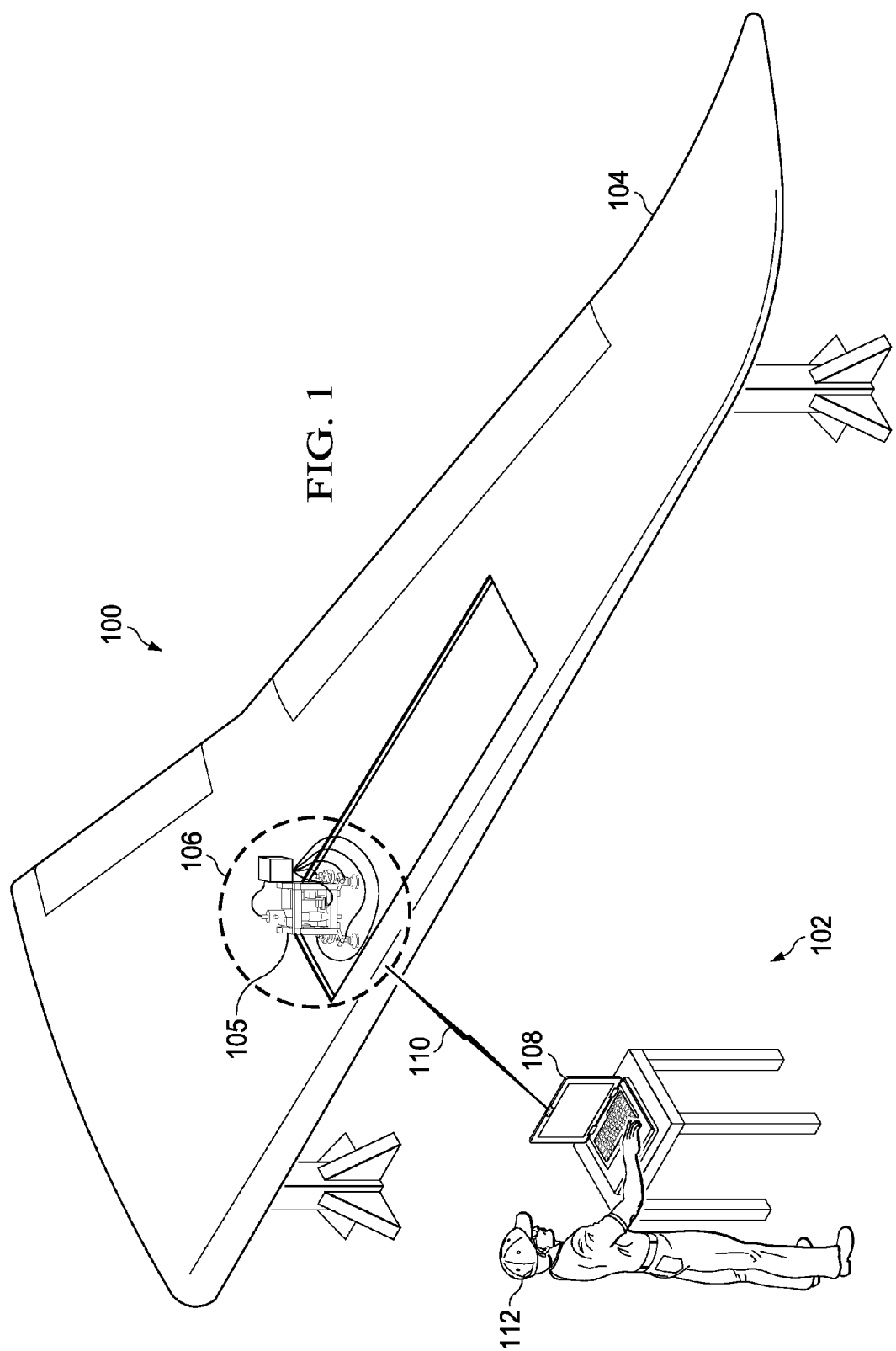
FIG. 1 is an illustration of a thermal sound inspection environment in accordance with an illustrative embodiment.

The illustrative embodiments recognize and take into account one or more different considerations. For example, ultrasonic thermography is an example of a type of inspection that may be used to detect inconsistencies in a composite structure. This type of inspection involves sending sound waves into the structure. The sound waves may take the form of ultrasonic excitation delivered by a vibrating device such as an ultrasonic welder or a shaker. The vibration in the structure may cause different types of motion in the area of the structure where an inconsistency is present. This type of motion may cause heat to occur in the area where the inconsistency is present. Other portions of the composite structure remain inert or will increase in temperature far less than the location where the inconsistency is present.

The increased temperature at the location may be caused by heating of an inconsistency that is at the surface or near the surface of the composite structure. The heat is detected at the surface of the composite structure. In this manner, the change in temperature caused by the heat may be detected through the use of an infrared camera.

Inconsistencies generate more heat than other portions of the composite structure that remain inert. As a result, images received by an infrared camera may be examined to identify a presence of inconsistencies in the composite structure. These inconsistencies may include disbonding, delamination, and other undesired inconsistencies.

The illustrative embodiments also recognize and take into account that the generation of inconsistencies within a structure may occur when changes to the structure are made. For example, the illustrative embodiments recognize and take into account that during the formation of holes, countersinks, and other features in a structure, inconsistencies may be generated in the structure that may be undesirable. As an example, inconsistencies such as delamination, cracks, and other undesired inconsistencies may be generated when forming features such as holes and countersinks in a composite structure.

The illustrative embodiments recognize and take into account that the use of thermal imaging in conjunction with sending sound signals, such as ultrasonic sound waves, into the area in which the countersink is present may provide more information about the inconsistency than ultrasonic testing in which ultrasonic echo response signals are analyzed. For example, the use of thermal imaging may be used to identify inconsistencies in the form of sequential delaminations. The illustrative embodiments also recognize and take into account that different portions of a countersink with an inconsistency may heat up at different times. Thus, the illustrative embodiments recognize and take into account that currently used thermal imaging in which an image is generated still may not identify the extent of the inconsistency as well as desired.

Thus, the illustrative embodiments provide a method and apparatus for inspecting a structure. In one illustrative example, images about the heat generated by a structure are received. In these illustrative examples, these images are a sequence of images capturing the heat generated by inconsistencies in response to sound signals. A final image is generated from the entire duration of images using areas of the images generating the greatest amount of heat emission.

In this manner, when different portions of a structure heat up at different times from sound waves propagating through the structure, the heat generated by inconsistencies may be more easily detected, with higher contrast. Further, the extent of the inconsistency in the structure may also be more easily detected.

With reference now to the figures and, in particular, with reference to FIG. 1, an illustration of a thermal sound inspection environment is depicted in accordance with an illustrative embodiment. As depicted, thermal sound inspection environment 100 is an environment in which thermal sound inspection system 102 may be used to inspect composite wing 104. In these illustrative examples, composite wing 104 may be comprised of various structures such as skin panels, spars, ribs, stringers, and other suitable structures.

As depicted, thermal inspection unit 105 in thermal sound inspection system 102 may be positioned relative to composite wing 104 at location 106. In this illustrative example, thermal inspection unit 105 is used to inspect composite wing 104 for inconsistencies.

Thermal inspection unit 105 is configured to generate sound signals in composite wing 104. Additionally, thermal sound inspection system 102 is configured to detect heat that may be generated by sound signals traveling within composite wing 104. The heat may be detected as differences in temperature that may be detected in different areas of composite wing 104 in location 106. The sound signals traveling within composite wing 104 may generate heat at inconsistencies within composite wing 104.

Thermal sound inspection system 102 is also configured to generate sequential images of areas of local heat emission in composite wing 104. Local heat emission is generated at inconsistencies in composite wing 104 by frictional heating in response to the external vibration excitation. Locations at which inconsistencies in composite wing 104 are present may generate more heat than other locations.

Thermal sound inspection system 102 generates a final image using areas of the sequence of images having the greatest amount of heat. Thermal sound inspection system 102 may generate this final image using a peak store algorithm or any other suitable type of process.

Thermal sound inspection system 102 may then send the final image to computer 108 in thermal sound inspection system 102 over wireless communications link 110. Of course, a wired communications link may be used in place of wireless communications link 110.

Wireless communications link 110 may be used in a large inspection area. Wireless communications link 110 also may be used in situations in which a supervising operator may review results obtained by other operators in the area in which inspections are being performed.

Computer 108 may display the final image. Operator 112 may view the image displayed on computer 108 to determine whether an inconsistency is present at location 106 of composite wing 104.

In other illustrative examples, computer 108 may perform an analysis to determine whether an inconsistency is present using the final image. This determination may then be displayed to operator 112.

In these illustrative examples, thermal sound inspection system 102 takes into account that different portions of composite wing 104 with one or more inconsistencies may heat up at different times in response to the sound signals launched within composite wing 104 by thermal inspection unit 105. In these illustrative examples, the sound signals may take the form of an excitation pulse within composite wing 104. By taking the areas of the images generated with the greatest amount of heat, a final image may be provided that allows for a better identification, through improved contrast, of the extent of one or more inconsistencies that may be present in composite wing 104.

In this manner, the extent of an inconsistency or multiple inconsistencies in location 106 on composite wing 104 may be identified in an efficient manner. This identification allows for a determination as to whether the inconsistency is an undesired inconsistency, whether rework is required, or whether a composite structure should be discarded.

Figure 2:
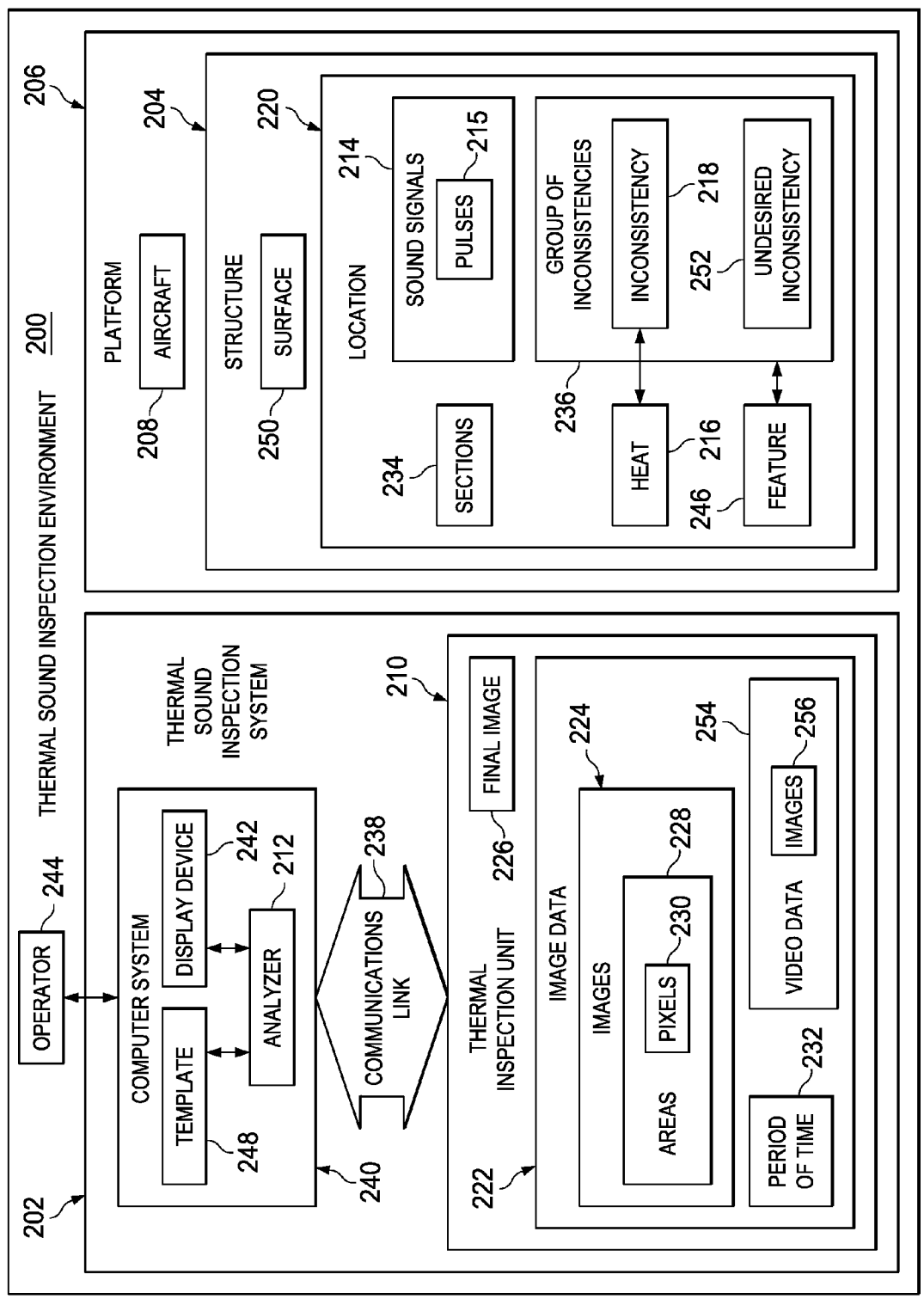
FIG. 2 is an illustration of a thermal sound inspection environment shown in block form in accordance with an illustrative embodiment.

With reference now to FIG. 2, an illustration of a thermal sound inspection environment shown in block form is depicted in accordance with an illustrative embodiment. Thermal sound inspection environment 100 is an example of one implementation for thermal sound inspection environment 200 in FIG. 2.

In this depicted example, thermal sound inspection system 202 may be used to perform an inspection of structure 204 in platform 206. This inspection may take the form of a thermal sound inspection. As depicted, platform 206 takes the form of aircraft 208.

Structure 204 may be, for example, composite wing 104 or one or more structures in composite wing 104 in FIG. 1 when platform 206 takes the form of aircraft 208. Of course, structure 204 may take other forms. For example, without limitation, structure 204 may be a fuselage, a horizontal stabilizer, a vertical stabilizer, a wingbox, a skin panel, a stringer, a spar, a rib, an engine housing, an engine inlet, a door, and other suitable types of structures. Structure 204 may be comprised of a material selected from at least one of a metal, a composite material, a plastic, wood, rubber, and other suitable types of materials.

As used herein, the phrase "at least one of," when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C. In other examples, "at least one of" may be, for example, without limitation, two of item A, one of item B, and ten of item C; four of item B and seven of item C; and other suitable combinations.

In this illustrative example, thermal sound inspection system 202 comprises thermal inspection unit 210 and analyzer 212. As depicted, thermal inspection unit 210 is configured to generate sound signals 214 in structure 204.

Sound signals 214 may be generated in pulses 215. Pulses 215 may be a number of pulses. Pulses 215 may be selected such that a desired amount of energy is generated by thermal inspection unit 210 to detect inconsistencies within structure 204 without generating additional inconsistencies in structure 204.

If pulses 215 of sound signals 214 are too long or the number of pulses 215 is too large, heat 216 at the excitation point may be generated to an extent that additional inconsistencies are created at the surface of structure 204. With currently used inspection systems, excitation may occur for a longer duration or at a higher energy level, increasing the potential for additional inconsistencies formed at the surface of the object under test.

The creation of additional inconsistencies at the surface of structure 204 may be reduced or avoided by reducing the length of pulses 215, the number of pulses 215, or both. In other words, with the use of an illustrative embodiment, the length of a pulse in pulses 215 of the ultrasonic sound waves is selected to reduce at least one of a generation of a new inconsistency and an increase in an extent of the inconsistency that is present in structure 204.

Sound signals 214 are configured to generate heat 216 in structure 204. In particular, sound signals 214 may be sound excitation in these illustrative examples. Sound excitation may be the vibration of structure 204 at ultrasonic frequencies. Heat 216 from this sound excitation is electromagnetic radiation that may be generated through the motion of particles or other components in structure 204.

When inconsistency 218 is present at location 220 of structure 204, heat 216 is generated. Typically, heat is not generated in other areas where inconsistency 218 is absent. The process of identifying inconsistency 218 may be considered to be a "dark field" thermography method when only inconsistency 218 generates heat 216 in location 220.

In some illustrative examples, heat 216 may be generated by other features other than inconsistency 218. For example, heat 216 may be generated in the location at which the excitation head of thermal sound inspection system 202 contacts structure 204. Heat 216 generated at attachment areas may be taken into account when inspecting structure 204. In other words, these areas where heat 216 is generated may not be considered in determining characteristics of inconsistency 218 at location 220 in these illustrative examples.

As depicted, heat 216 is generated by friction that may occur as a result of vibrations in inconsistency 218 in location 220 caused by sound signals 214. As a result, heat 216 generated by inconsistency 218 may be very local in these illustrative examples.

In these illustrative examples, thermal inspection unit 210 is configured to generate image data 222 about heat 216. In these examples, heat 216 is thermal energy that is generated from inconsistencies in the structure 204. In particular, heat 216 may be generated at surface 250 of structure 204 if inconsistency 218 is open to surface 250 or under surface 250.

In particular, thermal inspection unit 210 is configured to generate image data 222 in the form of images 224 about heat 216 at location 220. For example, images 224 may have brightness that indicates an amount of heat at location 220. Images 224 may be generated periodically and may be generated to form still images or a video.

Thermal inspection unit 210 is configured to generate final image 226 from images 224 using areas 228 of images 224 having a greatest amount of heat. In these illustrative examples, the greatest amount of heat is a maximum heat emission for a particular area in the different images in images 224. In this illustrative example, areas 228 may take the form of pixels 230. Of course, areas 228 may take other forms. For example, areas 228 may be groups of pixels or other forms depending on the particular implementation.

In these illustrative examples, images 224 are generated during period of time 232. Period of time 232 may be a period of time during which sound signals 214 propagate through structure 204. In this manner, areas 228 from images 224 used in final image 226 may originate from different images generated during different times during period of time 232. In these illustrative examples, images 224 are a sequence of images.

The generation of final image 226 takes into account that when inconsistency 218 extends through different sections 234 of structure 204, sections 234 may heat up with heat 216 at different times in period of time 232. As a result, different portions in sections 234 may have more heat and may be reflected in areas 228 across images 224 during period of time 232.

In some illustrative examples, additional image data may be generated by other camera systems in thermal inspection unit 210. For example, image data 222 generated by thermal inspection unit 210 also may be video data 254. Video data 254 may be in the form of images 256.

In these illustrative examples, inconsistency 218 may be an inconsistency within group of inconsistencies 236. As used herein, a "group of" when used with reference to items means one or more items. For example, group of inconsistencies 236 is one or more inconsistencies. When one or more additional inconsistencies are present in group of inconsistencies 236 in addition to inconsistency 218 in location 220, the one or more additional inconsistencies also may generate heat 216. Heat 216 from group of inconsistencies 236 including inconsistency 218 may be present in images 224 and final image 226.

In this illustrative example, analyzer 212 receives final image 226 from thermal inspection unit 210 over communications link 238. Communications link 238 may be a wired communications link, an optical communications link, a wireless communications link, or some other suitable type of communications link. Analyzer 212 is configured to process final image 226.

Analyzer 212 may be implemented using hardware, software, or a combination of the two. In these illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. As used herein, a "number of" when used with reference to items means one or more items. For example, a number of operations is one or more operations. The device may be reconfigured at a later time or may be permanently configured to perform the number of operations.

Examples of programmable logic devices include, for example, a programmable logic array, a programmable array logic, a field programmable logic array, a field programmable gate array, and other suitable hardware devices.

Additionally, the processes may be implemented in organic components integrated with inorganic components and/or may be comprised entirely of organic components excluding a human being. For example, the processes may be implemented as circuits in organic semiconductors.

In this illustrative example, analyzer 212 may be implemented in computer system 240. Computer system 240 is comprised of one or more computers. When more than one computer is present, those computers may be in communication with each other over a communications medium such as a network.

In this illustrative example, analyzer 212 may display final image 226 on display device 242 to operator 244. Display device 242 may be, for example, a liquid crystal display, a light-emitting diode display, a plasma display, or some other suitable hardware display device.

In this manner, operator 244 may analyze final image 226 to determine whether group of inconsistencies 236 is present in structure 204 in location 220. In these illustrative examples, group of inconsistencies 236 may be present in feature 246 in structure 204 at location 220. Group of inconsistencies 236 may be formed in feature 246 during the formation of feature 246.

Operator 244 also may determine whether an inconsistency in group of inconsistencies 236 is undesired inconsistency 252. In these illustrative examples, an inconsistency may be an undesired inconsistency or an inconsistency within selected tolerances. For example, inconsistency 218 may be undesired inconsistency 252 when inconsistency 218 has certain parameters.

For example, if inconsistency 218 does not have a greater than desired depth, inconsistency 218 is not considered to be undesired inconsistency 252. In other words, inconsistency 218 may be within desired depth tolerances for structure 204.

The depth at which inconsistency 218 may be present and not considered undesired inconsistency 252 may be based on factors such as design tolerances, rules, or other policies. The depth of inconsistency 218 may be used to determine the size and significance of rework when inconsistency 218 is undesired inconsistency 252.

When inconsistency 218 is undesired inconsistency 252, additional operations may be performed. Conversely, if inconsistency 218 is not undesired inconsistency 252, then rework, replacement, or other operations may be unnecessary. Instead, structure 204 may be suitable for use without rework or other changes.

In these illustrative examples, additional inconsistencies in group of inconsistencies 236 may be analyzed. As an additional inconsistency is analyzed, a determination is made as to whether the inconsistency has a depth that results in an undesired inconsistency or whether the depth of the inconsistency is within selected tolerances. This type of determination is unavailable with currently used techniques.

Feature 246 may be, for example, without limitation, at least one of a hole, a countersink, a scarf, or some other suitable feature. For example, when feature 246 is a hole with a countersink, group of inconsistencies 236 may be formed during drilling operations performed on structure 204 to form the hole with the countersink. Group of inconsistencies 236 may extend below surface 250 into the countersink in the hole in these illustrative examples. In this illustrative example, the countersink is formed downward from surface 250 of structure 204. Group of inconsistencies 236 may be located on the surface of the countersink formed in surface 250 of structure 204.

In these illustrative examples, a countersink may be a conical hole that is formed in surface 250 in structure 204. The countersink may be formed after an initial hole is formed through structure 204 or during the formation of the hole.

As depicted, analyzer 212 may be used to identify the extent of inconsistency 218 using template 248. In these illustrative examples, template 248 is a template for feature 246 and may be used to indicate the extent of inconsistency 218. This extent may be in terms of a depth below surface 250 as evident on the surface of the countersink of structure 204.

For example, with a countersink formed in a composite structure, different layers of composite material may be exposed on the surface of the countersink at different depths of the countersink below surface 250 of structure 204. When analyzer 212 processes portions of final image 226 closer to the center of the countersink in final image 226, the depth of inconsistency 218 increases. Thus, with the use of template 248, analyzer 212 may determine the depth of inconsistency 218.

Alternatively, operator 244 may use final image 226 to count the layers of the countersink in structure 204 to determine the depth of inconsistency 218. As operator 244 looks farther inward toward the center of the countersink while analyzing final image 226, the depth of inconsistency 218 increases. Each ring of final image 226 may represent a certain depth of the countersink. Thus, an operator may determine the depth of inconsistency 218 in the countersink by counting the rings in final image 226.

Although the illustrative embodiments have been shown with images 256 from video data 254 generated by thermal inspection unit 210, a visible light camera may be omitted from thermal inspection unit 210 depending on the particular implementation. Further, the use of a visible light camera to generate video data 254 in images 256 may provide additional views or other information about inconsistency 218 in structure 204 other than the depth of inconsistency 218 or other features determined by heat 216 generated by inconsistency 218. In other words, while an infrared camera system may generate final image 226 of inconsistency 218, a visible light camera may or may not be used to provide additional information about structure 204, inconsistency 218, or both in these illustrative examples.

Figure 3:
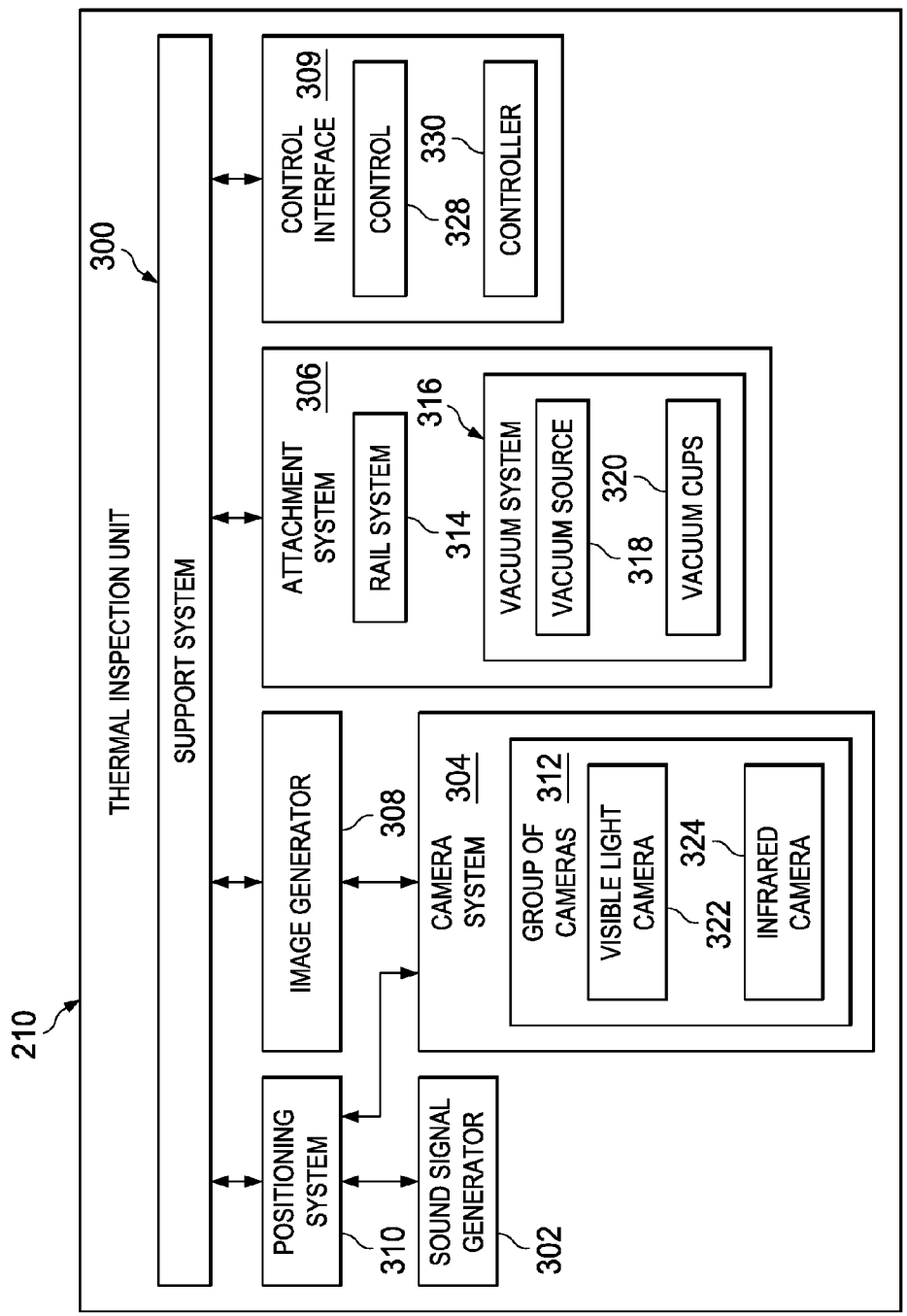
FIG. 3 is an illustration of a thermal inspection unit shown in block form in accordance with an illustrative embodiment.

With reference now to FIG. 3, an illustration of a thermal inspection unit shown in block form is depicted in accordance with an illustrative embodiment. One implementation for thermal inspection unit 210 is illustrated in this figure.

As depicted, thermal inspection unit 210 is comprised of a number of different components. For example, thermal inspection unit 210 may include support system 300, sound signal generator 302, camera system 304, attachment system 306, image generator 308, positioning system 310, and control interface 309.

As depicted, sound signal generator 302, camera system 304, attachment system 306, image generator 308, positioning system 310, and control interface 309 may be associated with support system 300. When one component is "associated" with another component, the association is a physical association in these depicted examples. For example, a first component, support system 300, may be considered to be associated with a second component, sound signal generator 302, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

In this illustrative example, support system 300 is configured to provide support for the different components in thermal inspection unit 210. Support system 300 may take various forms. For example, support system 300 may be a frame, a housing, or some other suitable structure.

In this illustrative example, sound signal generator 302 is configured to generate pulses of ultrasonic waves. In particular, sound signal generator 302 is configured to generate sound signals 214 in structure 204 in FIG. 2 in the form of pulses 215.

As depicted, sound signal generator 302 may be implemented using any device configured to generate sound signals 214 in pulses 215 in structure 204 in a manner such that heat 216 results from sound signals 214 in structure 204. In these illustrative examples, sound signal generator 302 may be selected from at least one of a piezoelectric transducer, a shaker, and other suitable types of devices such as ultrasonic welders. With the use of a shaker, a piezomechanical device is attached to surface 250 of structure 204. This device vibrates structure 204 to generate heat 216 from inconsistency 218 in structure 204.

In these illustrative examples, sound signal generator 302 may generate sound signals 214 in the form of ultrasonic waves. Ultrasonic waves may have frequencies from about 0.02 megahertz (MHz) to about 0.04 MHz. In other illustrative examples, other frequencies may be used when structure 204 takes the form of a composite structure. Of course, other frequencies may be used that are configured to generate heat 216 as a result of the propagation of sound signals 214 within structure 204 using the selected frequency or frequencies.

In this illustrative example, camera system 304 may be comprised of group of cameras 312. Group of cameras 312 may include visible light camera 322 and infrared camera 324. In some illustrative examples, visible light camera 322 may be omitted, depending on the particular implementation.

Infrared camera 324 may be implemented using any device that is configured to detect heat 216. In other words, infrared camera 324 may be selected to detect changes in temperature in structure 204. In these illustrative examples, group of cameras 312 may generate image data 222 for images 224 using infrared radiation. As depicted, group of cameras 312 in camera system 304 may detect infrared light such as light having a wavelength from about 3 microns to about 5 microns or from about 8 microns to about 12 microns. Of course, other wavelengths may be used depending on the particular camera used to implement group of cameras 312.

Visible light camera 322 may be implemented using any device that is configured to generate images from visible light. The images generated by visible light camera 322 are not images 224 or final image 226 that reveal inconsistency 218 in FIG. 2. Instead, visible light camera 322 may generate images 256 about some other feature of structure 204, depending on the particular implementation.

For example, visible light camera 322 may generate images using light having a wavelength from about 390 nanometers to about 750 nanometers. In some illustrative examples, visible light camera 322 may generate images for a video. In other illustrative examples, images generated by visible light camera 322 may be used for alignment of thermal inspection unit 210. Of course, in still other illustrative examples, images from visible light camera 322 may not be needed for alignment of thermal inspection unit 210.

Attachment system 306 is a device configured to attach support system 300 and the other components to structure 204. For example, attachment system 306 may take the form of at least one of rail system 314, vacuum system 316, and other suitable types of systems. For example, rail system 314 may be attached to holes, posts, and other features on structure 204. With rail system 314, support system 300 may be attached to structure 204 and moved to different locations such as location 220 on structure 204.

When vacuum system 316 is used, vacuum system 316 may comprise vacuum source 318 and vacuum cups 320. Vacuum source 318 generates a vacuum in vacuum cups 320. When a vacuum is generated by vacuum cups 320, vacuum cups 320 may hold support system 300 on surface 250 of structure 204 in FIG. 2.

Image generator 308 is configured to receive images 224 from camera system 304. Image generator 308 is configured to generate final image 226 from images 224. In particular, image generator 308 may select areas 228 from images 224 that have the highest amount of heat. For example, each area of final image 226 may be replaced with a corresponding area of an unprocessed image when the corresponding area of the unprocessed image has a greater brightness than the area of final image 226 that is currently present in final image 226.

In these illustrative examples, image generator 308 may be implemented using hardware, software, or a combination of the two. When hardware is present, image generator 308 may be implemented using circuits configured to compare an unprocessed image in images 224 to final image 226. Areas 228 of the unprocessed image having a greater brightness than the corresponding areas in final image 226 are replaced with those from the image being processed. In this manner, final image 226 collects the brightest values for areas 228 from sequence of images 224.

Positioning system 310 is a hardware device configured to manage the position of at least one of camera system 304 and sound signal generator 302 on support system 300. For example, positioning system 310 may be selected from at least one of a moveable cross bar, a robotic arm, an actuator, and other suitable components.

In these illustrative examples, positioning system 310 may be used to connect at least one of sound signal generator 302 and camera system 304 to support system 300. In still other illustrative examples, positioning system 310 may also connect image generator 308 to support system 300.

As depicted, control interface 309 may include control 328 and controller 330. Control interface 309 may allow operator 244 in FIG. 2 to initiate the inspection of structure 204. For example, control 328 may be a button configured to be pushed by operator 244. Controller 330 may be hardware that is configured to cause attachment system 306 to attach thermal inspection unit 210 to surface 250 of structure 204.

Additionally, controller 330 also may be configured to cause sound signal generator 302 to generate sound signals 214 and camera system 304 to generate images 224. Further, controller 330 may cause image generator 308 to generate final image 226 from images 224.

In these illustrative examples, all of these operations may be initiated by a single touch by operator 244 that actuates control 328. In other illustrative examples, control 328 may also allow operator 244 to make adjustments to various parameters used to generate sound signals 214 and images 224.

For example, in some illustrative examples, a frequency for sound signals 214 may be selected using control 328. A frequency range may be selected for a particular type of material for structure 204. This frequency range may be selected to cause sound signals 214 to "chirp" or "sweep."

In this case, the frequency for sound signals 214 may increase or decrease with time across a desired range of frequencies. In this manner, knowledge of a particular resonance character of structure 204, the inconsistencies, or both is not necessary.

In still other illustrative examples, a particular frequency may be selected based on certain characteristics of the materials in structure 204. As an example, characteristics of a material in structure 204 may be known to operator 244. With this knowledge, operator 244 may use control 328 to select a desired frequency for pulses 215 of sound signals 214.

Further, the particular frequency may be selected as one that provides a resonance for the inconsistency in the particular material under test. For example, using a selected frequency for a metal part with a specific resonance character may be useful in generating the final image of an inconsistency in the metal part. Of course, the frequency for pulses 215 of sound signals 214 may be pre-programmed and may be a single frequency for all materials tested, depending on the particular implementation.

As another example, the length of time for sound signals 214 or the number of pulses of sound signals 214 may be selected using control 328. In yet another illustrative example, a number of images 224 or the frequency at which images 224 are generated also may be selected using control 328.

The illustration of thermal sound inspection environment 200 and the different components in thermal sound inspection environment 200 in FIG. 2 and FIG. 3 are not mean to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, camera system 304 may be located on a separate support system from support system 300 in some illustrative examples. In yet other illustrative examples, attachment system 306 may be unnecessary. Instead, thermal inspection unit 210 may be moved and positioned relative to structure 204 by a robotic arm or some other suitable device. In some illustrative examples, thermal inspection unit 210 may take the form of an end effector for a robotic arm.

Additionally, in some illustrative examples, camera system 304 may not include visible light camera 322. In another example, camera system 304 may include one or more infrared cameras in addition to infrared camera 324.

In still other illustrative examples, final image 226 may be generated by analyzer 212 rather than thermal inspection unit 210. In this illustrative example, thermal inspection unit 210 sends images 224 to analyzer 212 for analysis.

Further, although image generator 308 is shown as a component in thermal inspection unit 210, image generator 308 may be implemented in other locations other than in thermal inspection unit 210. For example, image generator 308 may be implemented as part of analyzer 212 or another component in computer system 240 in FIG. 2 in these illustrative examples.

Figure 4:
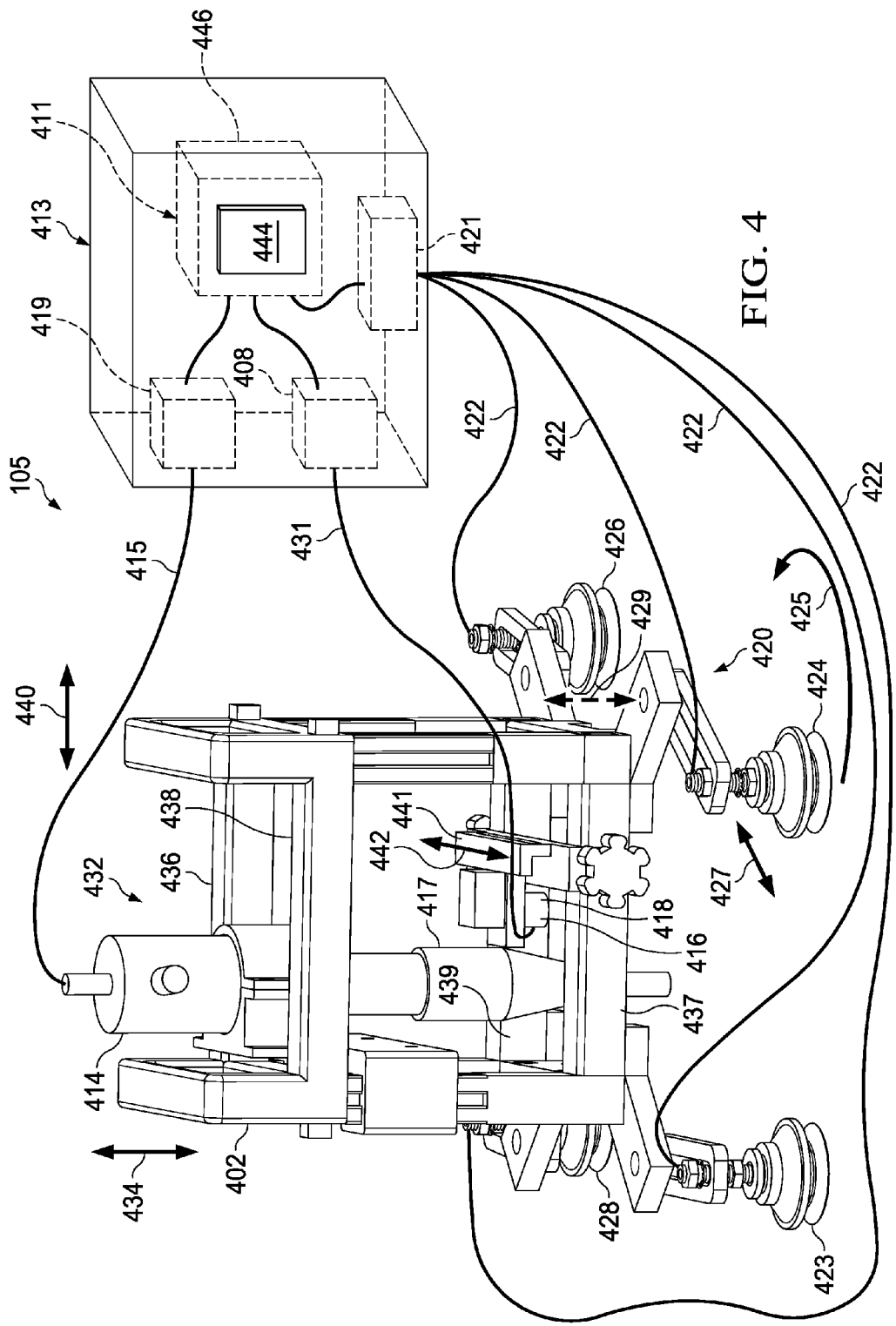
FIG. 4 is an illustration of a thermal inspection unit in accordance with an illustrative embodiment.

With reference now to FIG. 4, an illustration of a thermal inspection unit is depicted in accordance with an illustrative embodiment. In this illustrative example, a more detailed view of thermal inspection unit 105 in FIG. 1 is shown. In this illustrative example, thermal inspection unit 105 is an example of one physical implementation for thermal inspection unit 210 shown in block form in FIG. 2 and FIG. 3.

In this illustrative example, frame 402 is an example of an implementation for support system 300 in FIG. 3. In this illustrative example, frame 402 has a cuboid shape. Of course, frame 402 may have other shapes depending on the particular implementation. In this illustrative example, frame 402 provides support for the other components in thermal inspection unit 105.

In these illustrative examples, transducer controller 419 and ultrasonic transducer 414 are examples of components that may be used to implement sound signal generator 302 in FIG. 3. As depicted, transducer controller 419 is associated with housing 413 and ultrasonic transducer 414 is associated with frame 402. Transducer controller 419 is electrically connected to ultrasonic transducer 414 by wire 415. Transducer controller 419 is hardware that is configured to generate electrical signals that cause ultrasonic transducer 414 to generate ultrasonic signals. These ultrasonic signals may be in the form of one or more pulses.

Transducer controller 419 may send the electrical signals to ultrasonic transducer 414 through wire 415. Ultrasonic transducer 414 is a piezoelectric transducer and is connected to ultrasonic horn 417 in these illustrative examples. Ultrasonic horn 417 is the component that contacts the surface of the structure and transmits the ultrasonic sound signals generated by ultrasonic transducer 414 into the structure. In other illustrative examples, ultrasonic transducer 414 may be a shaker or some other suitable type of device.

In this illustrative example, infrared camera 416 and video camera 418 are associated with frame 402 and are examples of infrared camera 324 and visible light camera 322 in camera system 304 in FIG. 3. Infrared camera 416 is configured to generate images of heat that may be generated by a structure, such as structure 204 in FIG. 2. Video camera 418 is configured to generate images for a video using visible light in this illustrative example.

In this illustrative example, vacuum system 420 is an example of an implementation for vacuum system 316 in attachment system 306 in FIG. 3. Vacuum system 420 may attach frame 402 to a structure. In particular, vacuum system 420 includes vacuum pump 421, vacuum lines 422, vacuum cup 423, vacuum cup 424, vacuum cup 426, and vacuum cup 428. Vacuum system 420 is configured to generate a vacuum that attaches frame 402 to the surface of a structure, such as composite wing 104 in FIG. 1.

As depicted, vacuum cup 423, vacuum cup 424, vacuum cup 426, and vacuum cup 428 may move such that different configurations of vacuum cup 423, vacuum cup 424, vacuum cup 426, and vacuum cup 428 are present on surface 250 of structure 204. For example, vacuum cup 424 may rotate in the direction of arrow 425 about axis 429. In other illustrative examples, vacuum cup 424 may move in the direction of arrow 427. Similarly, vacuum cup 423, vacuum cup 426, and vacuum cup 428 may be adjusted in this manner.

In these illustrative examples, peak store detector 408 is associated with housing 413. Peak store detector 408 is an example of an implementation for image generator 308 in FIG. 3. Peak store detector 408 is a hardware circuit in this illustrative example. In particular, peak store detector 408 may be an analog hardware circuit. Peak store detector 408 stores pixels for images generated by infrared camera 416.

Peak store detector 408 is electrically connected to infrared camera 416 by wire 431 and receives images from infrared camera 416. Peak store detector 408 compares an image received from infrared camera 416 with an image currently stored in peak store detector 408. The comparison is between pixels in the image received from infrared camera 416 and the final image stored by peak store detector 408.

If a pixel in the image received from infrared camera 416 is brighter than the corresponding pixel stored in the final image by peak store detector 408, the pixel in the final image is replaced with the pixel in the image received. In particular, the replacement of the pixel is a replacement of the value with a new value for brightness in this illustrative example. In this manner, after some number of images are received from infrared camera 416, the final image stored by peak store detector 408 contains the brightest areas from each of the images.

In this manner, peak store detector 408 may generate a final image that takes into account the fact that different portions of a structure may heat up at different times in response to sound waves traveling through the structure. In these illustrative examples, an inconsistency at different depths on the surface of the countersink or inconsistencies of different sizes may result in the maximum heat emission occurring at different times. In other words, different inconsistencies may have a temperature that is higher at different times. As a result, different images may not capture the different locations in which inconsistencies may be present if the inconsistencies are different sizes or are located at different depths on the surface of the countersink.

In these illustrative examples, peak store detector 408 may be used to enable a short energy pulse to be used to excite the part rather than keep the excitation source energized while the inspection area is dispositioned in real time. For example, when an energy level of greater than about 400 Watts is used, the part may be rendered unusable.

Further, with peak store detector 408, all of the brightest pixels are accumulated in a manner without requiring ultrasonic transducer 414 being energized. Further, with peak store detector 408, the complexity and cost of thermal inspection unit 105 may be reduced. For example, a computer system for analyzing data is unnecessary. Instead, an operator may view the final image generated by peak store detector 408. Of course, a data processing system may still be used to provide further analysis depending on the particular implementation.

As depicted, rail system 432 is associated with frame 402 and is an example of an implementation for positioning system 301 in FIG. 3. Rail system 432 is physically connects ultrasonic transducer 414 and infrared camera 416 and video camera 418 to frame 402. As depicted, rail system 432 includes rail 436, rail 438, rail 437, and rail 439.

Ultrasonic transducer 414 is moveably connected to rail 436 and rail 438 and configured to move in the direction of arrow 440 between rail 436 and rail 438. Ultrasonic transducer 414 may move in the direction of arrow 434 on rail system 432.

Infrared camera 416 and video camera 418 are moveably connected to rail 437 and rail 439 by bar 441 and may be configured to move in the direction of arrow 440 between rail 437 and rail 439. Infrared camera 416 and video camera 418 may move in the direction of arrow 440 to provide a desired alignment for infrared camera 416 and video camera 418. Additionally, infrared camera 416 and video camera 418 may move in the direction of arrow 442 on bar 441.

Also, frame 402 moves in the direction of arrow 434 when a vacuum is pulled vacuum system 420 or when a vacuum is released by vacuum system 420. In particular, ultrasonic horn 417 is moved closer to surface 250 of structure 204 in FIG. 2 when a vacuum is pulled by vacuum system 420. In contrast, ultrasonic horn 417 is moved further away from surface 250 of structure 204 when the vacuum is released.

Control interface 411 is associated with housing 413. In this illustrative example, control interface 411 includes user interface 444 and controller 446. User interface 444 may be actuated by an operator to initiate inspection of a location on a structure. User interface 444 may take the form of a monitor which may have touch screen capability in this illustrative example.

As illustrated, when the operator interacts with user interface 444, controller 446 generates control signals to cause ultrasonic transducer 414 to activate. In response to the activation of ultrasonic transducer 414 by controller 446, infrared camera 416 generates images and peak store detector 408 operates to generate a final image from the images generated by infrared camera 416. Infrared camera 416 and peak store detector 408 operate passively to generate images from sound signals sent by ultrasonic transducer 414.

The final image generated by peak store detector 408 may be displayed on user interface 444 in these illustrative examples. In still other illustrative examples, controller 446 also may cause vacuum system 420 to activate.

Figure 5:
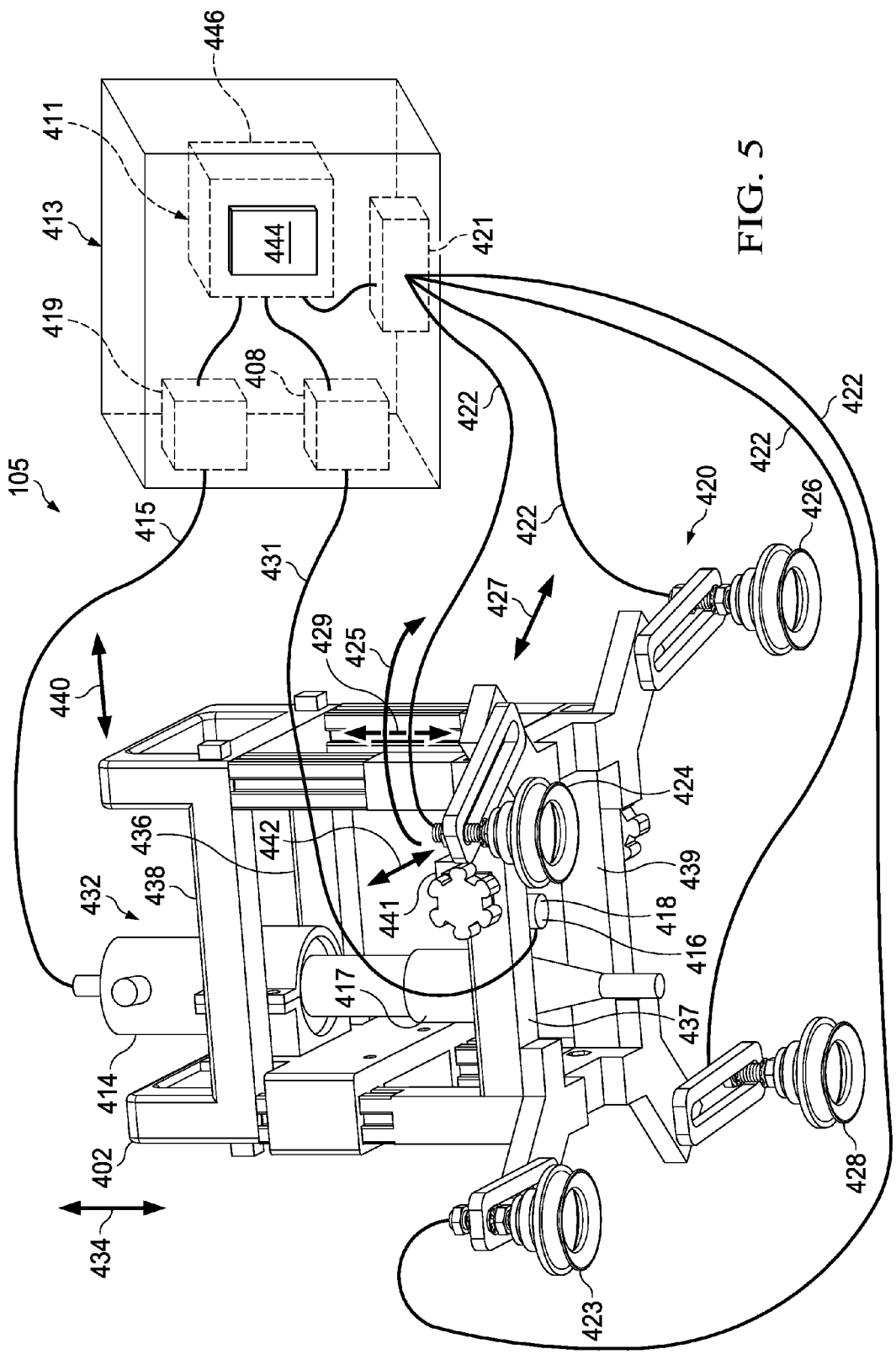
FIG. 5 is another illustration of a thermal inspection unit in accordance with an illustrative embodiment.

Turning now to FIG. 5, another illustration of a thermal inspection unit is depicted in accordance with an illustrative embodiment. Another isometric view of thermal inspection unit 105 is seen in this figure.

The illustrations of thermal inspection unit 105 in FIG. 1, FIG. 4, and FIG. 5 are not meant to imply physical or architectural limitations to the manner in which other thermal inspection units may be implemented. For example, in some illustrative examples, a housing may be used in place of frame 402. In still another illustrative example, video camera 418.

The different components shown in FIG. 1, FIG. 4, and FIG. 5 may be combined with components in FIG. 2 and FIG. 3, used with components in FIG. 2 and FIG. 3, or a combination of the two. Additionally, some of the components in FIG. 1, FIG. 4, and FIG. 5 may be illustrative examples of how components shown in block form in FIG. 2 and FIG. 3 can be implemented as physical structures.

Figure 6:
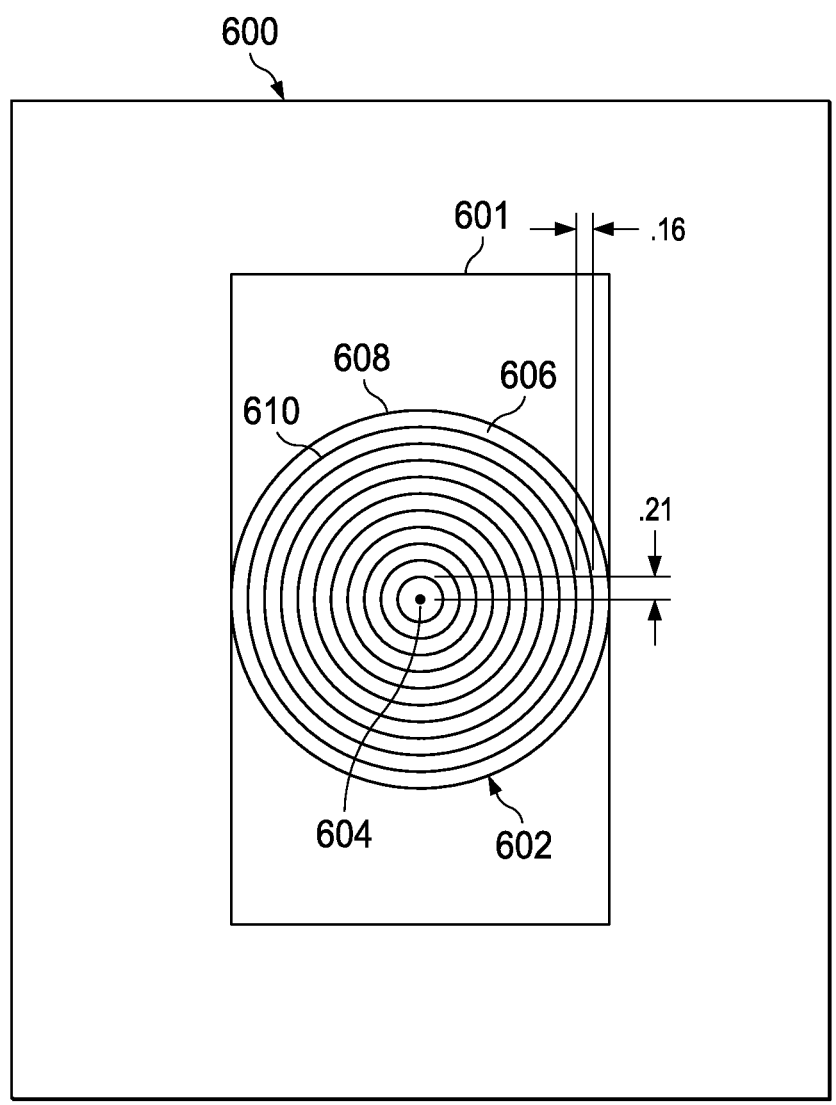
FIG. 6 is an illustration of a template in accordance with an illustrative embodiment.

Turning now to FIG. 6, an illustration of a template is depicted in accordance with an illustrative embodiment. In this illustrative example, template 600 is an example of one implementation for template 248 shown in block form in FIG. 2.

In this illustrative example, template 600 may be used to estimate the extent of a feature in the form of a countersink. In this illustrative example, template 600 may be implemented as a physical device or a graphical indicator for a display. As depicted, template 600 is comprised of planar structure 601 with concentric circles 602 around center point 604 on planar structure 601. Template 600 may be used with thermal inspection unit 210 to provide an estimate of a depth of an inconsistency, such as inconsistency 218 in FIG. 2.

Template 600 may be placed on a display device. In other illustrative examples, template 600 may be a graphical indicator that is displayed on the display device. As a result, final image 226 is displayed with template 600 on the display device.

As depicted, concentric circles 602 are present in template 600. Concentric circles 602 are displayed as being overlaid onto final image 226. Template 600 with concentric circles 602 provides a correlation to the depth of a surface in a countersink. The depth is indicated by the different circles in concentric circles 602.

In these illustrative examples, concentric circles 602 are configured to correspond to different depths on the surface of a countersink. In this illustrative example, gaps are present between concentric circles 602. Each gap may be equivalent to a depth in the countersink. For example, gap 606 between concentric circle 608 and concentric circle 610 may represent a change in depth of about 1.0 millimeters (mm) in the countersink.

In these illustrative examples, when template 600 is a hardware device placed on a display, template 600 may be comprised of a clear material such as plastic, poly(methyl methacrylate), polycarbonate, glass, or some other suitable material. Further, concentric circles 602 may be printed, etched, or otherwise formed on template 600.

When template 600 is a graphical indicator, template 600 may be added to final image 226 or may be displayed in conjunction with final image 226. For example, a software application may perform processing operations to determine the depth of inconsistency 218 in final image 226.

As a result of this processing, a value for the depth of inconsistency 218 at concentric circle 610 may be displayed on the display device. Similarly, a value for the depth of inconsistency 218 may be displayed on the display device when operator 244 selects a particular one of concentric circles 602.

In other illustrative examples, operator 244 may graphically draw a line across template 600 on the display device using a computer program and the software may measure the depth between one point on the line to another point on the line. In this manner, operator 244 may use template 600 to determine the depth of inconsistency 218 in the countersink in structure 204.

The illustration of template 600 is not meant to imply limitations to the manner in which templates may be implemented. In some illustrative examples, a template may have a different shape other than concentric circles 602 depending on the shape of the feature.

Figure 7:
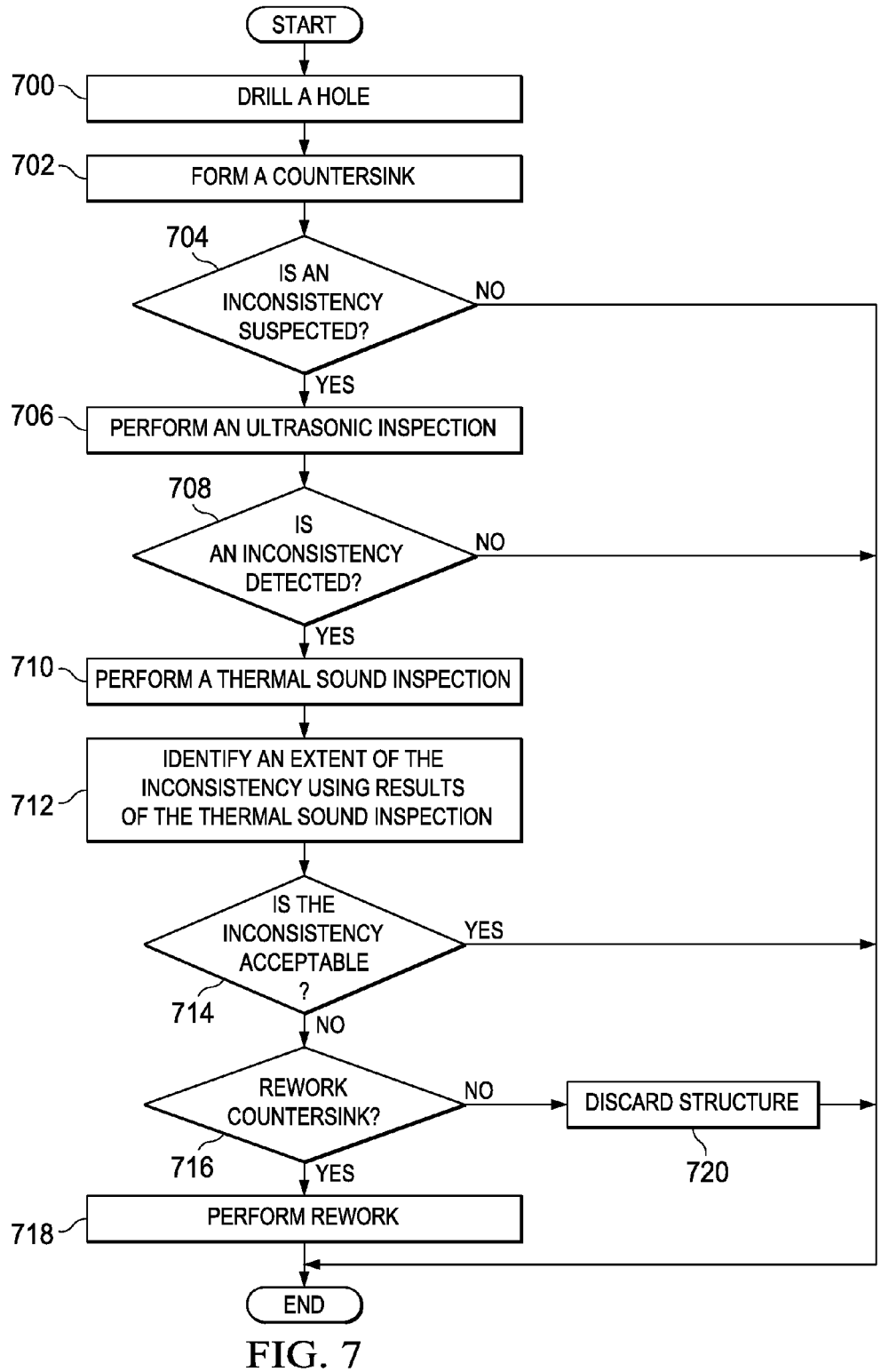
FIG. 7 is an illustration of a flowchart of a process for forming and inspecting a feature in accordance with an illustrative embodiment.

Turning now to FIG. 7, an illustration of a flowchart of a process for forming and inspecting a feature is depicted in accordance with an illustrative embodiment. In this illustrative example, the different operations in FIG. 7 may be used to form and inspect a countersink for a hole.

The process begins by drilling a hole(operation 700). Thereafter, the process forms a countersink (702). A determination is made as to whether an inconsistency is suspected in the countersink(operation 704). For example, smoke, a fracturing noise, a broken drill bit, overheating of a drill, or other abnormal operation or condition may indicate that an inconsistency may be present in the countersink.

If an inconsistency is suspected, an ultrasonic inspection is performed (operation 706). This inspection may be made using an ultrasound system having ultrasonic transducers. A determination is then made as to whether an inconsistency is detected using the results of the ultrasonic inspection (operation 708). If an inconsistency is detected, a thermal sound inspection is performed (operation 710). As depicted, operation 710 may be performed to identify inconsistencies beneath those detectable with the ultrasonic inspection. The thermal sound inspection may be performed using thermal sound inspection system 202 in FIG. 2.

The process identifies an extent of the inconsistency using results of the thermal sound inspection (operation 712). In operation 712, the extent of the inconsistency may be the dimensions of the inconsistency. The dimensions may include, for example, a width, a length, a depth, or some combination thereof. The depth may be estimated using a template such as template 248 in FIG. 2, and in particular, template 600 in FIG. 6.

A determination is then made as to whether the inconsistency is acceptable (operation 714). In operation 714, the inconsistency may be one identified by the ultrasonic inspection. In other illustrative examples, the inconsistency may be one in a group of inconsistencies identified by thermal sound inspection that may be present in addition to an initial inconsistency identified by the ultrasonic sound inspection. This determination may be made using tolerances or engineering margins for the structure associated with the countersink location. If the total number of inconsistencies, the depth of the inconsistencies, or both are acceptable, the process terminates and the hole with the countersink may be used in its current form.

Otherwise, a determination is made as whether the countersink can be reworked (operation 716). If the countersink can be reworked, the rework is performed (operation 718) with the process terminating thereafter. This rework may involve forming a scarf that removes material to the extent of the inconsistency detected. The scarf exposes layers of composite material down to the extent. In these illustrative examples, the scarf is formed to remove layers of composite material in which the inconsistency is located.

With reference again to operation 716, if the countersink cannot be reworked, the structure is discarded (operation 720) with the process terminating thereafter. Turning back to operation 708, if an inconsistency is not detected, the process terminates. Further, the process also terminates in operation 704 if an inconsistency is not suspected.

Figure 8:
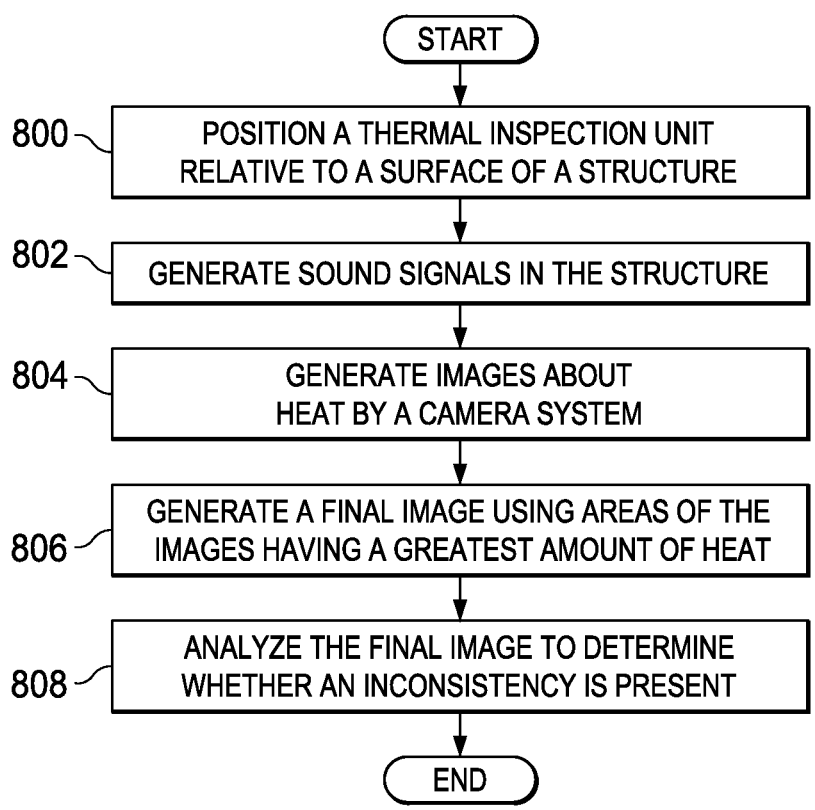
FIG. 8 is an illustration of a flowchart of a process for inspecting a structure in accordance with an illustrative embodiment.

With reference now to FIG. 8, an illustration of a flowchart of a process for inspecting a structure is depicted in accordance with an illustrative embodiment. The process illustrated in FIG. 8 may be implemented in thermal sound inspection environment 200 to inspect structure 204 in FIG. 2. In particular, the process may be implemented using thermal sound inspection system 202 and may be used to perform a thermal sound inspection of a structure.

The process begins by positioning a thermal inspection unit relative to a surface of a structure (operation 800). The positioning may, in some illustrative examples, include attaching the thermal inspection unit to the surface of the structure. In other illustrative examples, the thermal inspection unit may be held by another device such as a robotic arm.

The process then generates sound signals in the structure (operation 802). These sound signals are configured to cause heat to be generated within the structure. Images about heat are generated by a camera system (operation 804). This camera system may be, for example, an infrared camera system that is configured to detect the heat generated by the sound signals.

A final image is generated using areas of the images having a greatest amount of heat (operation 806). The final image is then analyzed to determine whether an inconsistency is present (operation 808) with the process terminating thereafter.

Figure 9:
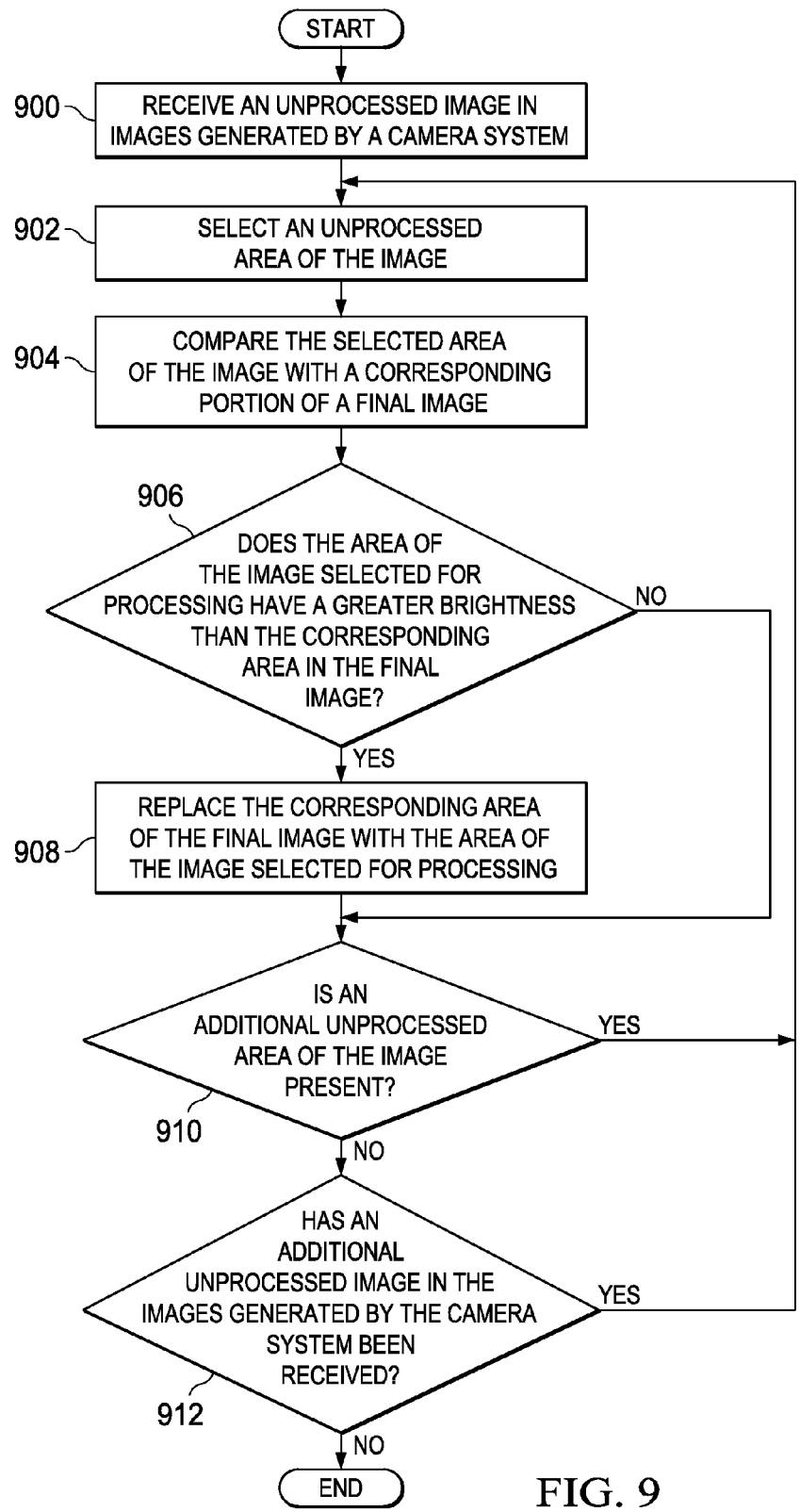
FIG. 9 is an illustration of a flowchart of a process for generating a final image in accordance with an illustrative embodiment.

Turning now to FIG. 9, an illustration of a flowchart of a process for generating a final image is depicted in accordance with an illustrative embodiment.

The process begins by receiving an unprocessed image in images generated by a camera system (operation 900). The process then selects an unprocessed area of the image (operation 902). This area may be a pixel, a grouping of pixels, or some other area of the image in these illustrative examples.

The process then compares the selected area of the image with a corresponding area of a final image (operation 904). A determination is made as to whether the area of the image selected for processing has a greater brightness than the corresponding area in the final image (operation 906). If the area of the selected image has a greater brightness, the corresponding area of the final image is replaced with the area of the image selected for processing (operation 908).

In this manner, the process is configured to generate a final image using areas of the image having a greatest amount of heat. With these different operations, each area of the final image is replaced with a corresponding area of the images when the corresponding area in the images has a greater brightness than each area of the final image. As a result, the final image is formed from areas of the images that have the greatest brightness.

In other words, all of the images that are generated are used to form the final image. Over the duration of time during which images are generated, all pixel locations on the final image are replaced by the brightest pixel that occurs during the period of time during which images are generated. In these illustrative examples, the brightest pixel corresponds to the hottest pixel. As a result, the brightest pixels that occur over the duration of image accumulation are registered on the final image.

A determination is then made as to whether an additional unprocessed area of the image is present (operation 910). If an additional unprocessed area is present, the process returns to operation 902. Otherwise, if an additional unprocessed area of the image is not present, a determination is made as to whether an additional unprocessed image in the images generated by the camera system has been received for processing (operation 912). If an additional unprocessed image has been received, the process returns to operation 902. Otherwise, the process terminates.

With reference again to operation 906, if the area of the image selected for processing does not have a greater brightness than the corresponding area in the final image, the process proceeds to operation 910.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

In one illustrative example, operation 802 and operation 804 may be performed at substantially the same time or these operations may be performed such that they overlap in time. In another example, operation 706 may be omitted and operation 710 may be performed when an inconsistency is suspected. In another illustrative example, the different operations in FIG. 7 may be performed for other types of features other than countersinks. For example, the different operations may be performed on holes.

Turning now to FIG. 10, an illustration of a block diagram of a data processing system is depicted in accordance with an illustrative embodiment. Data processing system 1000 may be used to implement computer 108 and computer system 240. In this illustrative example, data processing system 1000 includes communications framework 1002, which provides communications between processor unit 1004, memory 1006, persistent storage 1008, communications unit 1010, input/output (I/O) unit 1012, and display 1014. In this example, communication framework may take the form of a bus system.

Processor unit 1004 serves to execute instructions for software that may be loaded into memory 1006. Processor unit 1004 may be a group of processors, a multi-processor core, or some other type of processor, depending on the particular implementation.

Memory 1006 and persistent storage 1008 are examples of storage devices 1016. A storage device is any piece of hardware that is capable of storing information, such as, for example, without limitation, data, program code in functional form, and/or other suitable information either on a temporary basis and/or a permanent basis. Storage devices 1016 may also be referred to as computer readable storage devices in these illustrative examples. Memory 1006, in these examples, may be, for example, a random access memory or any other suitable volatile or non-volatile storage device. Persistent storage 1008 may take various forms, depending on the particular implementation.

For example, persistent storage 1008 may contain one or more components or devices. For example, persistent storage 1008 may be a hard drive, a flash memory, a rewritable optical disk, a rewritable magnetic tape, or some combination of the above. The media used by persistent storage 1008 also may be removable. For example, a removable hard drive may be used for persistent storage 1008.

Communications unit 1010, in these illustrative examples, provides for communications with other data processing systems or devices. In these illustrative examples, communications unit 1010 is a network interface card.

Input/output unit 1012 allows for input and output of data with other devices that may be connected to data processing system 1000. For example, input/output unit 1012 may provide a connection for user input through a keyboard, a mouse, and/or some other suitable input device. Further, input/output unit 1012 may send output to a printer. Display 1014 provides a mechanism to display information to a user.

Instructions for the operating system, applications, and/or programs may be located in storage devices 1016, which are in communication with processor unit 1004 through communications framework 1002. The processes of the different embodiments may be performed by processor unit 1004 using computer-implemented instructions, which may be located in a memory, such as memory 1006.

These instructions are referred to as program code, computer usable program code, or computer readable program code that may be read and executed by a processor in processor unit 1004. The program code in the different embodiments may be embodied on different physical or computer readable storage media, such as memory 1006 or persistent storage 1008.

Program code 1018 is located in a functional form on computer readable media 1020 that is selectively removable and may be loaded onto or transferred to data processing system 1000 for execution by processor unit 1004. Program code 1018 and computer readable media 1020 form computer program product 1022 in these illustrative examples. In one example, computer readable media 1020 may be computer readable storage media 1024 or computer readable signal media 1026.

In these illustrative examples, computer readable storage media 1024 is a physical or tangible storage device used to store program code 1018 rather than a medium that propagates or transmits program code 1018.

Alternatively, program code 1018 may be transferred to data processing system 1000 using computer readable signal media 1026. Computer readable signal media 1026 may be, for example, a propagated data signal containing program code 1018. For example, computer readable signal media 1026 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1000 are not meant to provide architectural limitations to the manner in which different embodiments may be implemented. The different illustrative embodiments may be implemented in a data processing system including components in addition to and/or in place of those illustrated for data processing system 1000. Other components shown in FIG. 10 can be varied from the illustrative examples shown. The different embodiments may be implemented using any hardware device or system capable of running program code 1018.

Illustrative embodiments of the disclosure may be described in the context of aircraft manufacturing and service method 1100 as shown in FIG. 11 and aircraft 1200 as shown in FIG. 12. Turning first to FIG. 11, an illustration of an aircraft manufacturing and service method is depicted in accordance with an illustrative embodiment. During pre-production, aircraft manufacturing and service method 1100 may include specification and design 1102 of aircraft 1200 in FIG. 12 and material procurement 1104.

During production, component and subassembly manufacturing 1106 and system integration 1108 of aircraft 1200 in FIG. 12 takes place. Thereafter, aircraft 1200 in FIG. 12 may go through certification and delivery 1110 in order to be placed in service 1112. While in service 1112 by a customer, aircraft 1200 in FIG. 12 is scheduled for routine maintenance and service 1114, which may include modification, reconfiguration, refurbishment, and other maintenance or service.

Each of the processes of aircraft manufacturing and service method 1100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 12, an illustration of an aircraft is depicted in which an illustrative embodiment may be implemented. In this example, aircraft 1200 is produced by aircraft manufacturing and service method 1100 in FIG. 11 and may include airframe 1202 with plurality of systems 1204 and interior 1206. Examples of systems 1204 include one or more of propulsion system 1208, electrical system 1210, hydraulic system 1212, and environmental system 1214. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1100 in FIG. 11. An illustrative embodiment may be used during components and subassembly manufacturing 1106 to inspect different structures manufactured for aircraft 1200. Further, an illustrative embodiment also may be used during maintenance and service 1114 to perform inspections on existing structures in aircraft 1200. Further, an illustrative embodiment also may be used during maintenance and service 1114 to inspect replacement structures, new structures, or other structures that may be used during routine maintenance, upgrades, refurbishment, and other operations. The use of a number of the different illustrative embodiments may substantially expedite the assembly of and/or reduce the cost of aircraft 1200.

Thus, the illustrative embodiments may be used to perform inspections of structures to identify inconsistencies. Further, with one or more illustrative embodiments, an extent of an inconsistency may be identified. For example, the depth of an inconsistency may be identified in a feature such as a countersink, a hole, or some other suitable feature. Further, these inspections may be performed in locations where features are absent.

Moreover, a thermal sound inspection system may be used to detect inconsistencies on different types of materials. For example, the thermal sound inspection system may be used with composite structures, fiberglass, para-aramid synthetic fiber, metal, or other suitable types of materials. With the use of a thermal sound inspection system on a metal structure, additional processing may be performed by an analyzer or other computer program to determine whether inconsistencies are present in the metal structure because of the conductive properties of that structure.

With the use of a thermal sound inspection system in accordance with an illustrative embodiment, a more complete identification of the number of inconsistencies in a countersunk hole may be made as compared to currently used techniques. In other words, the actual number of inconsistencies in a group of inconsistencies may be more accurately identified. In addition, the depth of an inconsistency on a surface of a feature also may be identified. Further, with this type of inspection, the amount of rework may be reduced.

For example, currently, when an inconsistency is identified, rework may be performed merely to remove the identified inconsistency. After the identified inconsistency is removed, further ultrasonic inspection may be performed to determine whether additional inconsistencies are present beyond the depth of the inconsistency previously identified with ultrasonic methods.

With an illustrative embodiment, an identification of the presence or absence of further inconsistencies may result in the countersink area of the hole being classified as being in an acceptable condition. In other words, a feature, such as a countersink, may still meet engineering specifications with the originally-detected inconsistency when further inconsistencies are either minor or absent. As a result, rework for an inconsistency may be avoided in some cases.

Further, with the use of a thermal sound inspection system in accordance with an illustrative embodiment, pulses of ultrasonic waves generated by the thermal sound inspection system may result in higher resolution images of inconsistencies present in the structure. For example, the use of pulses of ultrasonic waves generates images that show an arrangement of rings of heat. This arrangement of rings allows for analysis of the depth of the inconsistency present in the structure.

With currently used techniques that generate a constant amount of energy directed at the structure, images of the inconsistency may not be as accurate as desired. In other words, currently used techniques may be able to determine that an inconsistency is present in the structure but may not generate images accurate enough to detect particular characteristics of the inconsistency.

As an example, the images generated may not show rings for the different layers of composite material in the countersink. The heat detected may be a single blur or section in the image. With an illustrative embodiment, more accurate images are generated from the pulses of energy and thus, more accurate planning and execution of rework of the structure may be completed.

In addition, with the use of pulses of ultrasonic waves, additional inconsistencies may be avoided. For example, when using a thermal sound inspection system with an undesired or constant level of energy, the level or duration of energy may be such that additional inconsistencies on the surface of the structure may occur.

With the use of an illustrative embodiment, pulses of ultrasonic waves may provide the desired images for inspection and may prevent inconsistencies from occurring on the surface of the structure due to higher levels of energy, duration of the energy applied to the structure, or both. In other words, smaller amounts of energy may be used for a shorter period of time to provide a desired image of the inconsistencies present in the structure. The peak store detector used in the illustrative embodiments captures optimum heat emissions and provides better contrast in the final image.

Moreover, with the use of an illustrative embodiment, heat is generated at the edges of the countersink and as time passes, heat may be generated in deeper portions of the countersink. This feature allows a relatively low energy, short duration pulse to provide an adequate amount of energy to form a final image showing the inconsistencies in the structure.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a sound signal generator configured to generate sound signals configured to generate heat in a structure;
a camera system configured to detect the heat and generate image data about the heat; and
an image generator configured to receive images from the camera system and generate a final image of a countersink on a display device using areas of the images having a greatest amount of heat;
wherein the structure is a composite structure having layers of composite material and the countersink is formed in a portion of the layers of composite material;
wherein a characteristic of an inconsistency is determined from the final image of the countersink and a template, wherein the characteristic of the inconsistency comprises a depth of the inconsistency, wherein the template comprises a planar structure with concentric circles having gaps therebetween, wherein the gaps are based on a depth in the countersink, wherein the template provides a correlation between the final image and the depth of the inconsistency, wherein the template comprises a clear material, and wherein the template is configured to be placed on the display device.

2. The apparatus of claim 1, wherein in being configured to generate the final image using the areas of the images having the greatest amount of heat, the image generator is configured to replace each area of the final image with a corresponding area of an unprocessed image in the images when the corresponding area in the unprocessed image has a greater brightness than the each area of the final image;
wherein the template is placed on the display device; and
wherein the clear material is selected from one of plastic, poly methyl methacrylate, polycarbonate, and glass, and the concentric circles are one of printed, etched, or formed on the template.

3. The apparatus of claim 1 further comprising:
a support system, wherein the sound signal generator, the camera system, and the image generator are associated with the support system.

4. The apparatus of claim 3 further comprising:
an attachment system configured to attach the support system to the structure, wherein the attachment system comprises a vacuum system, vacuum cups, and a vacuum source.

5. The apparatus of claim 1, wherein the sound signal generator is configured to generate a number of pulses of ultrasonic sound waves.

6. The apparatus of claim 1, wherein the camera system is configured to generate video data.

7. The apparatus of claim 1 further comprising:
a controller configured to control operation of at least one of the sound signal generator, the camera system, and the image generator.

8. The apparatus of claim 1 further comprising:
a computer system in communication with the image generator, wherein the computer system is configured to identify an extent of the inconsistency using the final image.

9. The apparatus of claim 8, wherein the computer system is configured to identify the extent of the inconsistency in a feature in the structure using the final image and the template for the feature.

10. The apparatus of claim 5, wherein a length of a pulse in the number of pulses of the ultrasonic sound waves is selected to reduce at least one of a generation of a new inconsistency and an increase in an extent of an inconsistency.

11. The apparatus of claim 1, wherein the sound signal generator is selected from one of a piezoelectric transducer and a shaker.

12. The apparatus of claim 1, wherein the areas are pixels.

13. The apparatus of claim 1, wherein the structure is comprised of at least one of a composite material, metal, plastic, wood, and rubber.

14. A method for inspecting a structure, the method comprising:
receiving images of heat generated by an inconsistency in the structure;
generating a final image of a countersink on a display device from the images using areas of the images having a greatest amount of heat;
wherein the structure is a composite structure having layers of composite material and the countersink is formed in a portion of the layers of composite material; and
wherein a characteristic of the inconsistency is determined from the final image of the countersink;
wherein the characteristic of the inconsistency comprises a depth of the inconsistency; and
placing a template on the display device;
wherein the template comprises a planar structure with concentric circles that provide a correlation between the final image and the depth of the inconsistency in the countersink;
wherein the concentric circles have gaps therebetween such that the gaps are based on a depth of the countersink;
wherein the template comprises a clear material selected from one of plastic, poly methyl methacrylate, polycarbonate, and glass, and the concentric circles are one of printed, etched, or formed on the template.

15. The method of claim 14, wherein the generating step comprises:
replacing each area of the final image with a corresponding area of an unprocessed image in the images when the corresponding area in the unprocessed image has a greater brightness than the each area of the final image.

16. The method of claim 15 further comprising:
repeating the replacing step for each of the images.

17. The method of claim 14 further comprising:
generating the images during a period of time when sound signals are propagating through the structure.

18. The method of claim 14 further comprising:
generating sound signals in the structure.

19. The method of claim 14 further comprising:
identifying an extent of the inconsistency in a feature in the structure using the final image and a template for the feature.

20. The apparatus of claim 9, further comprising:
a control that, when actuated, initiates
the generation of the sound signals by the sound signal generator,
the generation of the image data by the camera system, and
the generation of the final image;
wherein the countersink is a conical hole that is formed in a surface in the structure one of after an initial hole is formed through the structure or during formation of the initial hole.

21. The apparatus of claim 20,
wherein the template with the concentric circles provides a correlation to a depth of a surface in the countersink, the depth of the surface in the countersink is indicated by different circles in concentric circles;
wherein the concentric circles are configured to correspond to different depths on the surface of the countersink;
wherein gaps are present between the concentric circles and each gap is equivalent to the depth in the countersink; and
wherein one of the gaps represents a change in depth of about 1.0 millimeters (mm) in the countersink.

22. The apparatus of claim 20,
wherein the template comprises the concentric circles around a center point;
wherein the template further comprises a graphical indicator displayed on the display device so that the final image is displayed with the template on the display device;
wherein the concentric circles are overlaid onto the final image;
wherein the concentric circles are configured to correspond to different depths on the surface of the countersink;
wherein each gap is equivalent to the depth in the countersink;
wherein one of the gaps represent a change in depth of about 1.0 millimeters (mm) in the countersink;
wherein the template is added to the final image from which the depth of the inconsistency in the final image is determined;
wherein a value for the depth of the inconsistency at one of the concentric circles is displayed on the display device;
wherein the value for the depth of the inconsistency is displayed on the display device after selection of a particular one of the concentric circles; and
wherein a line is graphically drawn on the template on the display device by an operator and a depth between one point on the line to another point on the line is measured by a computer program to determine the depth of the inconsistency in the countersink in the structure.

* * * * *